US011399577B2

United States Patent
Akerson et al.

(10) Patent No.: US 11,399,577 B2
(45) Date of Patent: Aug. 2, 2022

(54) NURSING GARMENT

(71) Applicant: Akerson IP LLC, Las Vegas, NV (US)

(72) Inventors: Deeanne Akerson, Oceanside, CA (US); Garret Akerson, Oceanside, CA (US)

(73) Assignee: AKERSON IP LLC, Las Vegas, NV (US)

( * ) Notice: Subject to any disclaimer, the term of this patent is extended or adjusted under 35 U.S.C. 154(b) by 282 days.

(21) Appl. No.: 16/745,719

(22) Filed: Jan. 17, 2020

(65) Prior Publication Data
US 2020/0146365 A1      May 14, 2020

Related U.S. Application Data

(63) Continuation of application No. 15/694,988, filed on Sep. 4, 2017, now Pat. No. 10,537,141.

(60) Provisional application No. 62/383,457, filed on Sep. 4, 2016.

(51) Int. Cl.

| A41C 3/04 | (2006.01) |
|---|---|
| A41C 3/12 | (2006.01) |
| A61B 5/00 | (2006.01) |
| G04F 10/00 | (2006.01) |
| A41C 3/00 | (2006.01) |
| A41C 3/02 | (2006.01) |
| A41D 1/215 | (2018.01) |

(52) U.S. Cl.
CPC ............ *A41C 3/04* (2013.01); *A41C 3/0021* (2013.01); *A41C 3/02* (2013.01); *A41C 3/12* (2013.01); *A61B 5/0024* (2013.01); *A61B 5/4288* (2013.01); *A61B 5/6804* (2013.01); *A61B 5/7282* (2013.01); *G04F 10/00* (2013.01); *A41D 1/215* (2018.01)

(58) Field of Classification Search
CPC ......... A41C 3/004; A41C 3/0021; A41C 3/02; A41C 3/12; A61B 5/0024; A61B 5/4288; A61B 5/6804; A61B 5/7282; G04F 10/00
USPC .......................................................... 450/36
See application file for complete search history.

(56) References Cited

U.S. PATENT DOCUMENTS

| 4,335,728 | A | * | 6/1982 | Fildan ...................... A41C 3/04 450/36 |
| 5,624,296 | A | * | 4/1997 | Weber-Unger .......... A41C 3/04 2/101 |
| 6,083,079 | A | * | 7/2000 | Pearson ................... A41C 3/00 450/1 |
| 6,165,047 | A | | 12/2000 | Scott et al. |
| 6,227,936 | B1 | * | 5/2001 | Mendoza ................. A41C 3/04 2/104 |

(Continued)

*Primary Examiner* — Gloria M Hale
(74) *Attorney, Agent, or Firm* — Diederiks & Whitelaw, PLC.

(57) ABSTRACT

A nursing garment computing system includes a nursing garment having a pair of breast cups with an electronic sensor to indicate the status of a breast in the pair of breast cups and a computing device to record the sensor data indicative of whether the breast cup is open or closed. The data can be electronically sent to an external device such as a cell phone or personal digital assistant to keep track of which breast cup has been opened for breastfeeding event, time between breastfeeding event, amount of time for breastfeeding from each side of the breast, a record of which side was nursed last, and a record of which side was nursed first during the last breastfeeding event.

18 Claims, 13 Drawing Sheets

(56) References Cited

U.S. PATENT DOCUMENTS

| | | | |
|---|---|---|---|
| 6,364,739 B1* | 4/2002 | Dutka | A41C 3/04 450/36 |
| 6,645,041 B2* | 11/2003 | Sørensen | D04B 1/246 450/36 |
| 7,094,217 B2 | 8/2006 | Fialkoff | |
| 8,057,452 B2 | 11/2011 | Fialkoff | |
| 8,192,247 B2 | 6/2012 | Abbaszadeh | |
| 8,307,463 B2 | 11/2012 | Ritchie | |
| 8,469,770 B2 | 6/2013 | Alva | |
| 8,657,643 B2 | 2/2014 | Perez | |
| 9,155,339 B2 | 10/2015 | Alva | |
| 9,167,855 B2 | 10/2015 | Abbaszadeh | |
| 9,402,425 B2 | 8/2016 | Cortese et al. | |
| 9,498,005 B2 | 11/2016 | Abbaszadeh | |
| 9,629,396 B2 | 4/2017 | Alva | |
| 9,872,524 B2 | 1/2018 | Abbaszadeh | |
| 9,894,942 B2 | 2/2018 | Burrell | |
| 10,231,491 B2* | 3/2019 | Akerson | A61B 5/6804 |
| 2005/0085160 A1* | 4/2005 | Johnstone | A41C 3/04 450/36 |
| 2008/0003921 A1* | 1/2008 | Fildan | A41C 3/04 450/36 |
| 2009/0265830 A1* | 10/2009 | Hendrickson | A41D 1/215 2/104 |
| 2010/0068971 A1* | 3/2010 | Hendrickson | A41C 3/04 450/31 |
| 2010/0159801 A1 | 6/2010 | Abbaszadeh | |
| 2010/0159802 A1 | 6/2010 | Abbaszadeh | |
| 2010/0261410 A1* | 10/2010 | Hirtz | A41C 3/04 450/36 |
| 2013/0095727 A1 | 4/2013 | Abbaszadeh | |
| 2014/0273737 A1* | 9/2014 | Cortese | A41C 3/04 450/31 |
| 2014/0364035 A1 | 12/2014 | Abbaszadeh | |
| 2014/0364036 A1 | 12/2014 | Abbaszadeh | |
| 2016/0015092 A1 | 1/2016 | Abbaszadeh | |
| 2016/0150834 A1* | 6/2016 | Boele | A41C 3/0035 450/36 |
| 2016/0183602 A1* | 6/2016 | Rider | A41C 3/04 450/36 |
| 2016/0206007 A1 | 7/2016 | Op'T Hof | |
| 2016/0331045 A1 | 11/2016 | Cortese et al. | |
| 2017/0273366 A1 | 9/2017 | Hoth | |
| 2017/0280786 A1 | 10/2017 | Abbaszadeh | |
| 2018/0000168 A1 | 1/2018 | Alva | |
| 2018/0064177 A1* | 3/2018 | Akerson | A61B 5/7282 |
| 2018/0064178 A1* | 3/2018 | Akerson | A61B 5/4288 |
| 2018/0092408 A1 | 4/2018 | Hensel | |
| 2018/0103691 A1 | 4/2018 | Alva | |
| 2018/0132542 A1 | 5/2018 | Abbaszadeh | |
| 2018/0206559 A1 | 7/2018 | Kosak | |
| 2019/0037931 A1* | 2/2019 | Akerson | A61B 5/4288 |

* cited by examiner

NURSING GARMENT

CROSS REFERENCE TO RELATED APPLICATIONS

This application represents a continuation application of U.S. patent application Ser. No. 15/694,988, filed Sep. 4, 2017, now U.S. Pat. No. 10,537,141, which claims the benefit of U.S. Provisional Patent Application No. 62/383,457, entitled "Nursing Garment", filed on Sep. 4, 2016, which is incorporated by reference herein in its entirety and for all purposes.

TECHNICAL FIELD

This invention generally relates to a nursing garment and more specifically to a nursing garment with electronic sensors to keep track of the breastfeeding event and breastfeeding time, as well as providing an electronic record that a breastfeeding mother can provide to her doctor and lactation consultant to make sure that their advice regarding nursing is based on full and complete information.

BACKGROUND

Breastfeeding of a baby by a nursing woman has important benefits including nutrition, immunity to illnesses and psychological factors such as mother/baby bonding. Additional benefits of breastfeeding include (for the baby): breastmilk is easier for baby to digest and is "made to order" (breastmilk composition changes as baby ages and even throughout the day to meet growing baby's needs exactly), associated with increased IQ, decreased risk of obesity, decreased risk of childhood cancers and illnesses (asthma, diabetes, heart disease, ear infections), decreased risk of SIDS, and increased bonding between mother and baby.

Proper support for mother and baby are necessary to ensure a successful breastfeeding relationship. Some common factors leading to early ending of breastfeeding include lack of support (by family, lactation consultants, or medical providers), latching issues (resulting in poor weight gain or destruction of mother's breast tissue further leading to pain and infection), difficulty establishing and maintaining a healthy breastmilk supply, and the mother returning to work with minimal workplace support or provision for pumping of breastmilk. Without proper support, breastfeeding attempts are often unsuccessful in the long-term, leading to the breastfeeding relationship ending earlier than is decided by the mother-baby dyad.

Risks of not breastfeeding include (for the mother): increased risk of obesity, increased risk of blood pressure instability, return of menstrual cycle possibly leading to closely spaced pregnancy and lack of conservation of nutrients, increased rate of postpartum depression, increased sleep disturbances, increased risk of breast and ovarian cancer, increased risk of cardiovascular disease, increased risk of type 2 diabetes, increased risk of Rheumatoid arthritis, and osteoporosis. Additional negative effects of unsuccessful breastfeeding are: working mothers missing more work days due to increase in the baby being sick, increased cost due to purchase of formula, and increase in health expenses due to decreased health.

These benefits and risks are well documented in scientific theory and literature.

In the recent days, there is an ever-growing awareness among nursing women concerning difficulties encountered while breastfeeding. An oft-stated goal has been to reduce breastfeeding-related problems and physical discomfort, and at the same time ensure an equal and adequate feeding of milk from both breasts. The feeding pattern more commonly practiced is feeding the baby from both breasts in a single feeding session. After the baby has fed from a breast for a period of time, the nursing woman switches the baby to the other breast and allows the baby to finish feeding on the other breast. It remains a major problem for breastfeeding mothers to keep track of how long a time span has passed since she fed the baby. An even more specific desirable measurement would be how much time has passed as measured by the time that has passed since the beginning of the last breastfeeding session.

Further, it is important to monitor and measure the amount of milk the baby has consumed in a feeding session. Generally, it is not easy for the nursing women to remember from which breast the baby last fed, thereafter neglecting the other breast and allowing it to become painfully engorged with milk. Thus, it is desirable to monitor the feeding time and keep track of the breast from which the baby last fed, how long the baby has been feeding on a breast, how long each feeding session lasts and the interval of time between the feedings. Indeed, lactation consultants and doctors rely on a breastfeeding mother's notes regarding the frequency and duration of the feeding sessions during the first few weeks of a baby's life to analyze the patterns and monitor the baby's weight to keep track of the weight gain. Thus, to have a more reliable means to keep track of interval times is highly desirable, as mistakes made in keeping notes may lead to incorrect medical decisions based on incomplete or incorrect data.

Breastfeeding bras have been known in the prior art for decades, and there are a number of breastfeeding bras on the market today that function quite well in allowing a woman to unfasten all, or a portion of a cup to nurse a baby. However, an unsolved problem is how a woman (and her doctors and lactation consultants) can keep track of the time that has elapsed since a woman has last nursed from either side, as well as recording which side was last nursed, and which side was first nursed during the last nursing session and how long she has nursed from either side. It is also important that a woman keep in mind not only how long she has nursed from each side to "balance" nursing between the two breasts, but also to time the nursing so that the baby nurses completely at one breast before being offered the other.

Thus, there has existed a long-felt need for a nursing garment which keeps track of the breast from which the baby last fed and the time interval between feedings, and the elapsed time on each breast of the current feeding session.

Therefore, the present invention aims to resolve the aforementioned issued by providing a nursing bra or other nursing garment with two cups, each of which can be opened to allow a baby access to a breast, where each cup has some means of electronic monitoring the duration of time the cup has been opened. Further, the feeding information data is stored in one or more smaller, lightweight electronic storage devices built into or attached to the nursing garment. Information can be downloaded via Bluetooth or another electronic means onto a cell phone or other personal digital assistant. This information can be used by the mother and/or given to a doctor or lactation consultant so that they can better determine a nursing regime for the nursing mother.

SUMMARY

It is therefore an object of the invention to provide a nursing garment that can monitor nursing time, record the date and time of each nursing session, record which side was nursed from last, record which side was nursed from first during the last nursing, record the amount of time that has elapsed since the last nursing, and nursing related measurements.

Additional objects of the invention include a nursing garment with the ability to record data and communicate with an external device.

Further objects of the invention include providing a nursing bra or other garment that, for a reasonable price, can track the nursing of a child to benefit the health of both mother and baby.

According to one aspect of the invention includes a nursing garment with partially removable breast cups, additionally comprising electronic means of determining when each breast cup is opened for breastfeeding. Preferably there is an electronic circuit that is either created, or disrupted, as a breast cup is opened.

According to another aspect of the invention includes a computing device or other computerized data retention and processing device that records the changes noted by the electronic circuit(s).

According to a preferred aspect of the invention a nursing garment computing system includes a nursing garment for breasts support having a pair of breast cups, shoulder straps and a body support. Further a pair of clips clasping each shoulder strap configured with a clasp sensor to generate data of a state of a breast in the pair of breast cups and a computing device to record clasp sensor data indicative of whether the breast cup is open.

According to another preferred aspect of the invention a wire is electronically connected to the clasp sensor and the computing device for transmitting of the clasp sensor data to the computing device. The computing device records the clasp sensor data, the clasp sensor data is indicative of the amount of time when the breast cup is open, thus starts counting the breastfeeding time. Further, the computing device transmits the clasp sensor data to an external device where the data can be downloaded via Bluetooth or another electronic means onto cell phone or other personal digital assistant device.

According to another preferred aspect of the invention the clasp sensor data is indicative of the amount of time each breast cup is open when the clip is unclasped and is also indicative of when a breastfeeding event occurs.

According to another preferred aspect of the invention the clasp sensor is programed for each breast cup, the clasp sensor data is recorded by the computing device identifies which breast cup is unclasped and thus the computing device start to keep track of the breastfeeding time for each breast.

According to another preferred aspect the nursing garment computing system includes a nursing garment having a pair of breast cups with an electronic sensor to indicate the status of a breast in the pair of breast cups and a computing device to record the sensor data indicative of whether the breast cup is open or closed. The data can be electronically sent to an external device such as a cell phone or personal digital assistant to keep track of which breast cup has been opened for a breastfeeding event, time between breastfeeding events, amount of time for breastfeeding from each side of the breast, a record of which side was nursed last, and a record of which side was nursed first during the last breastfeeding event.

Further another aspect of the invention the computing device records one or more breastfeeding events in response to the when a breast cup is opened and then closed.

Further another aspect of the invention when the clip is unclasped to lower a breast cup for breastfeeding, the connection of the clasp sensor and the computing device is affected and a breastfeeding event is recognized by the computing device, further, the computing device records the clasp sensor data, the clasp sensor data is indicative of the amount of time each breast cup is open, thus starts counting as "breastfeeding time" for purposes of data collection.

Further another aspect of the invention the computing device detects the clasp sensor within a specified, preprogrammed distance, such that when the clip is unclasped and lowered for breastfeeding, the clasp sensor is moved to a closer proximity to the computing device, the computing device records the amount of time the breast cup is open.

In short, a key component of this invention is to allow a woman to electronically and accurately keep track of how long a particular bra cup has been open for breastfeeding. The invention also allows a user of the invention to keep track of the intervals between breastfeeding events. She can use this information for her own scheduling of nursing sessions, and to provide to her doctor and lactation consultant so that they can advise her based on complete and accurate information.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

BRIEF DESCRIPTION OF THE DRAWINGS

This application will be described with reference to the following drawings. The drawings and the associated descriptions are provided to illustrate embodiments of the invention and not to limit the scope of the invention.

DETAILED DESCRIPTION

The term "clasped" is defined as connected or attached, although not necessarily directly, and not necessarily mechanically. The term "unclasped" is defined as detached or opened. The term "nursing" is defined as breastfeeding, which, in turn, can relate to pumping or expressing of milk. The terms "a" and "an" are defined as one or more unless this disclosure explicitly requires otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs.

The present invention now will be described more fully hereinafter with reference to the accompanying drawings, in which some, but not all embodiments of the inventions are shown. While the following description details the preferred embodiments of the present invention, this patent application is not limited in its application to the details of construction and arrangement of the parts illustrated in the accompanying drawings.

With reference to the figures, numerical designation has been given for each element to facilitate the reader's understanding of the present invention, and particularly with reference to the embodiments of the present invention illustrated in the figures; various preferred embodiments of the present invention are set forth below. The enclosed description and drawings are merely illustrative of preferred embodiments and represent several different ways of configuring the present invention. Although specific components, materials, configurations and uses of the present invention are illustrated and set forth in this disclosure, it should be understood that a number of variations to the components and to the configuration of those components described herein and in the accompanying figures can be made without changing the scope and function of the invention set forth herein.

Figure 1:
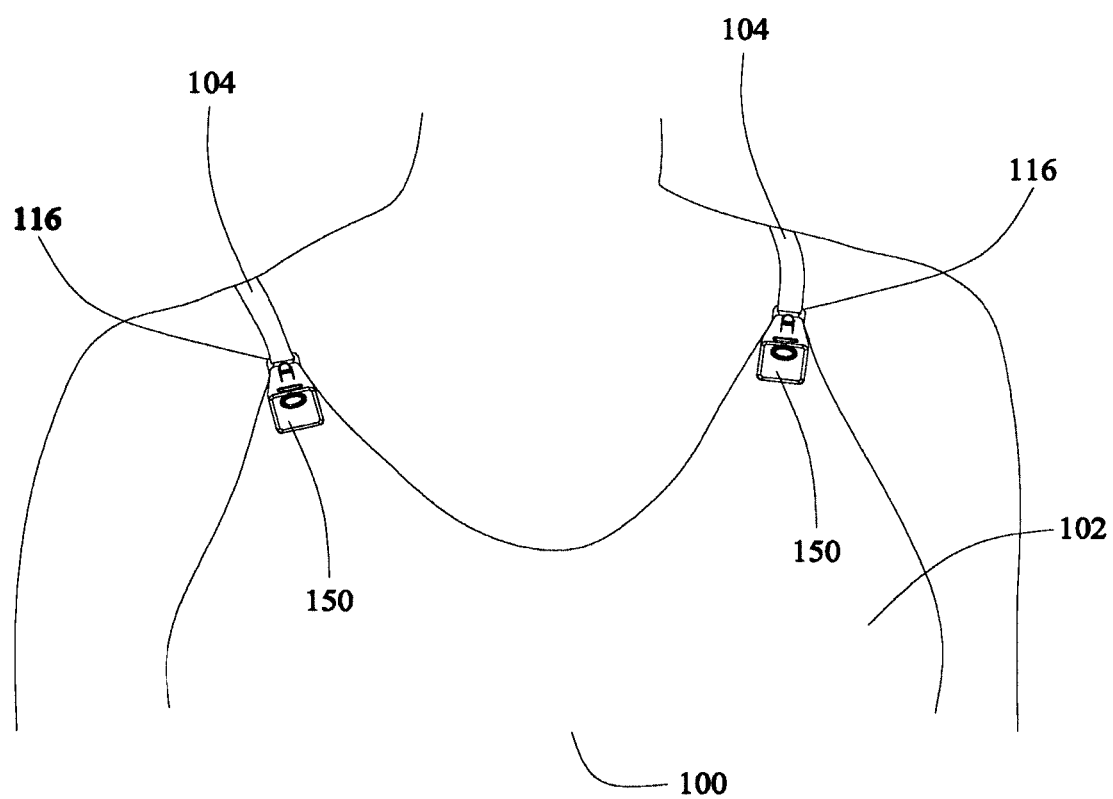
FIG. 1 is perspective view of a nursing garment computing system in accordance with an embodiment of the present invention.

Referring now to figures, in an exemplary embodiment of the present invention, a nursing garment computing system is described herein. As shown in the FIG. 1, FIG. 2 and FIG. 3, the nursing garment computing system, generally referenced as 100, is depicted as a brassiere or bra that permits a nursing woman to breastfeed/nurse a baby without removing the garment 100. However, it should be appreciated that the nursing garment 100 may be otherwise embodied. For example, in some embodiments, the nursing garment 100 may be embodied as a nursing bra but is not limited to a nursing bra, but rather includes but is not limited to a nursing top, a nursing shirt, nursing tank, nursing camisole, nursing dress or other item of clothing used for breastfeeding that includes the features described herein and/or is otherwise capable of performing the functions described herein. The nursing garment computing system 100 includes a breast support having a pair of breast cups 102, shoulder straps 104 and a body support having a front portion connected extending through side portions to a back portion, the front portion connecting to a middle section and each of the pair of breast cups 102, the side portion connecting to the front portion with one side portion connecting to one each of the pair of breast cups 102 that may be opened and closed to permit selective breastfeeding/nursing without removing the garment 100. That is, a nursing woman may wear the nursing garment 100 throughout the day and, when it is necessary to breastfeed to a baby, the breast cups 102 may be opened or unclasped to permit breastfeeding.

Figure 3:
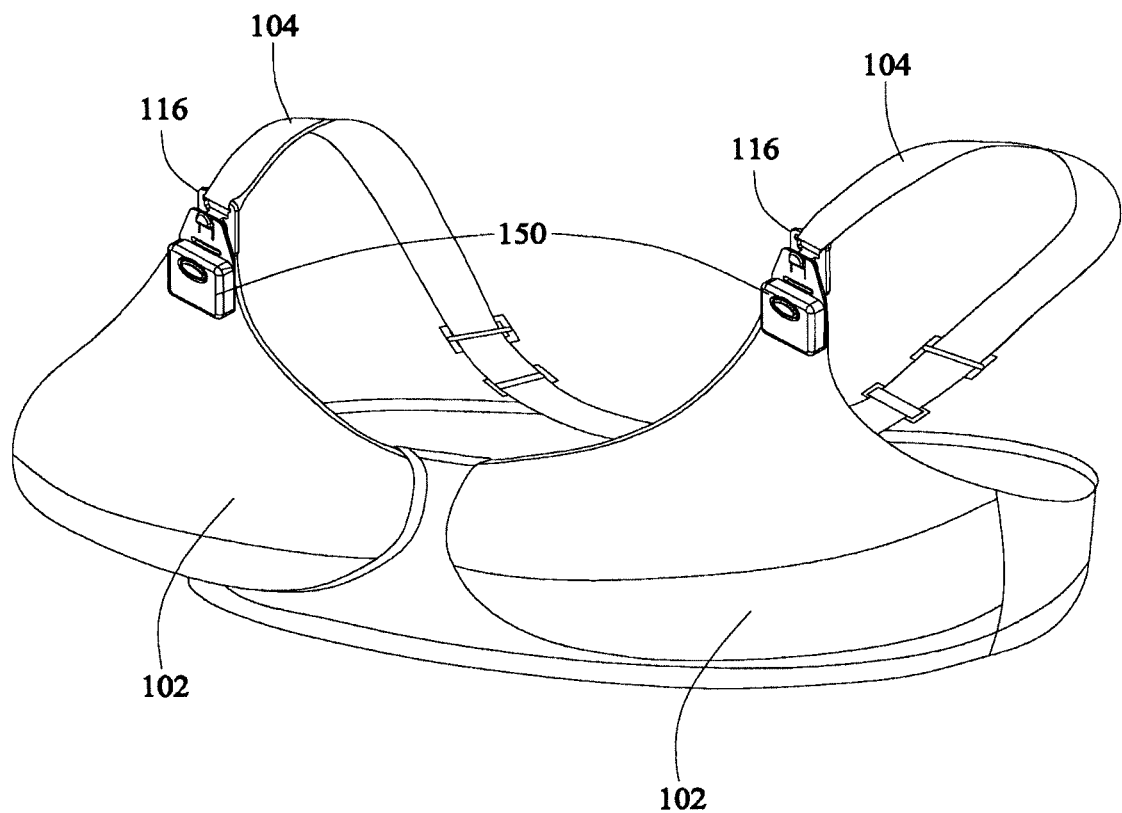
FIG. 3 is a perspective view of a nursing garment in accordance with another embodiment of the present invention.
Figure 4:
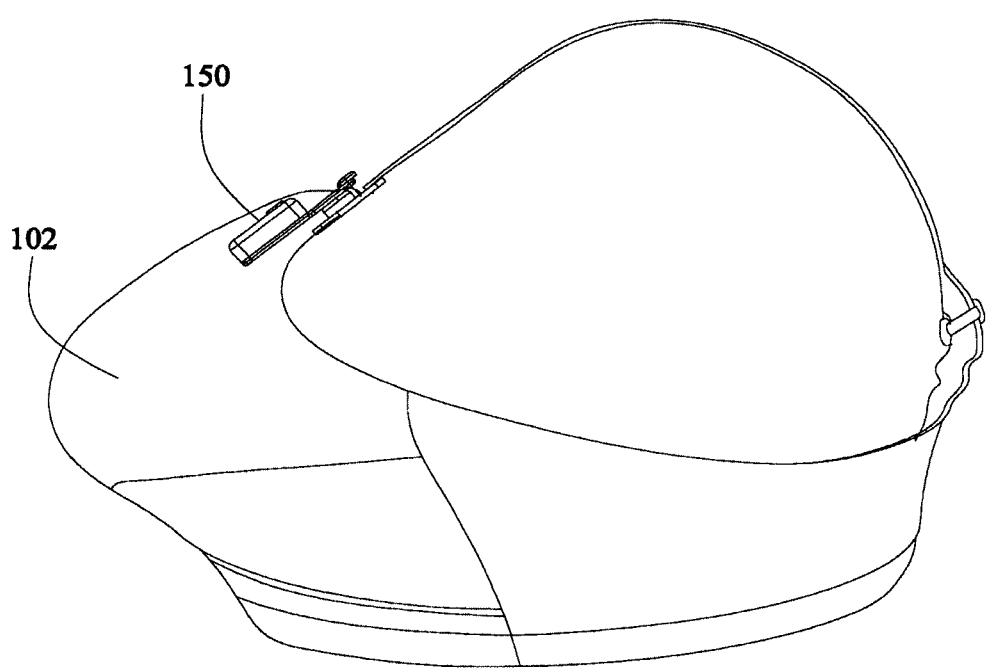
FIG. 4 is side view of the nursing garment computing system in accordance with an embodiment of the present invention.
Figure 5:
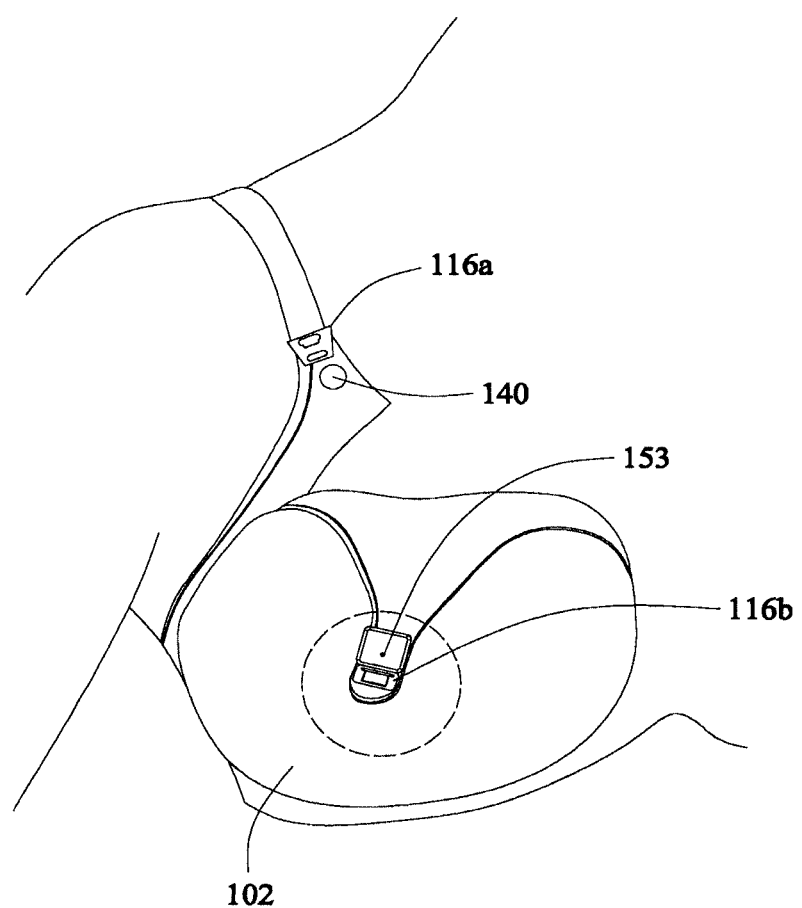
FIG. 5 is a perspective view of a nursing garment computing system in accordance with an embodiment of the present invention
Figure 6:
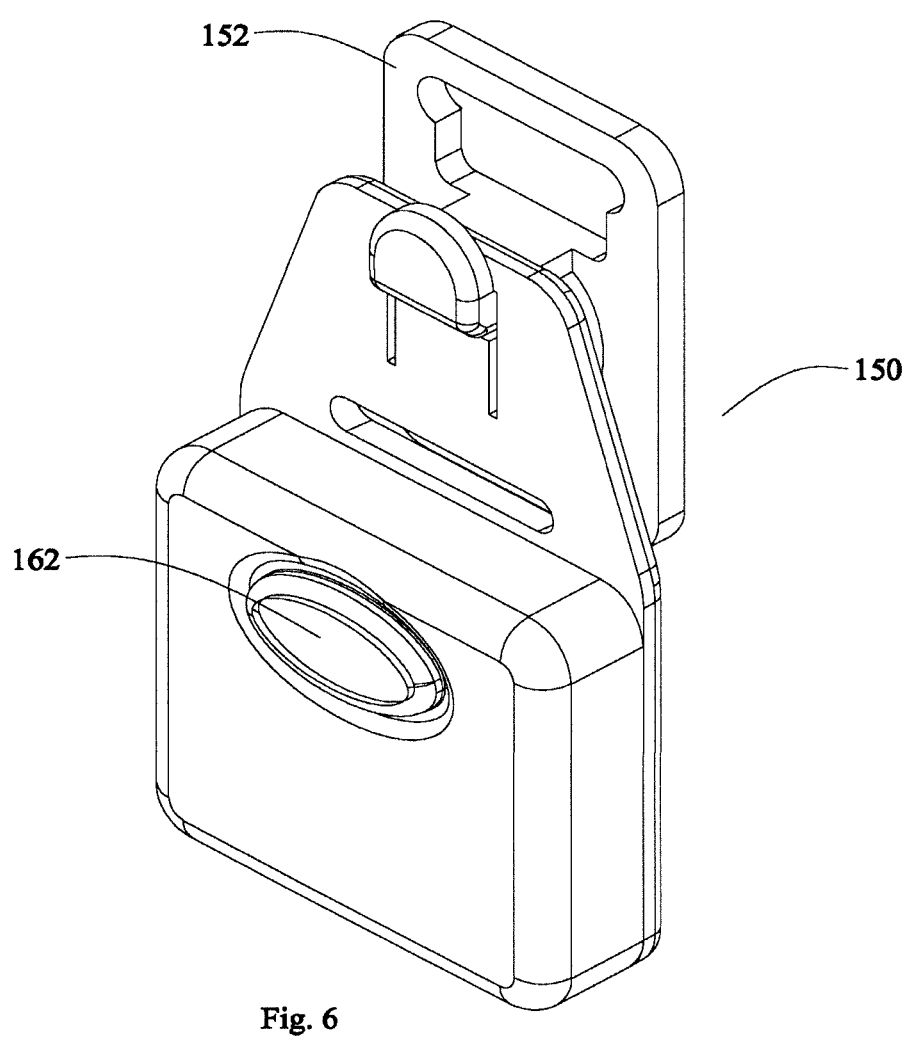
FIG. 6 is a perspective view of a computing device in accordance with an embodiment of the present invention.
Figure 7:
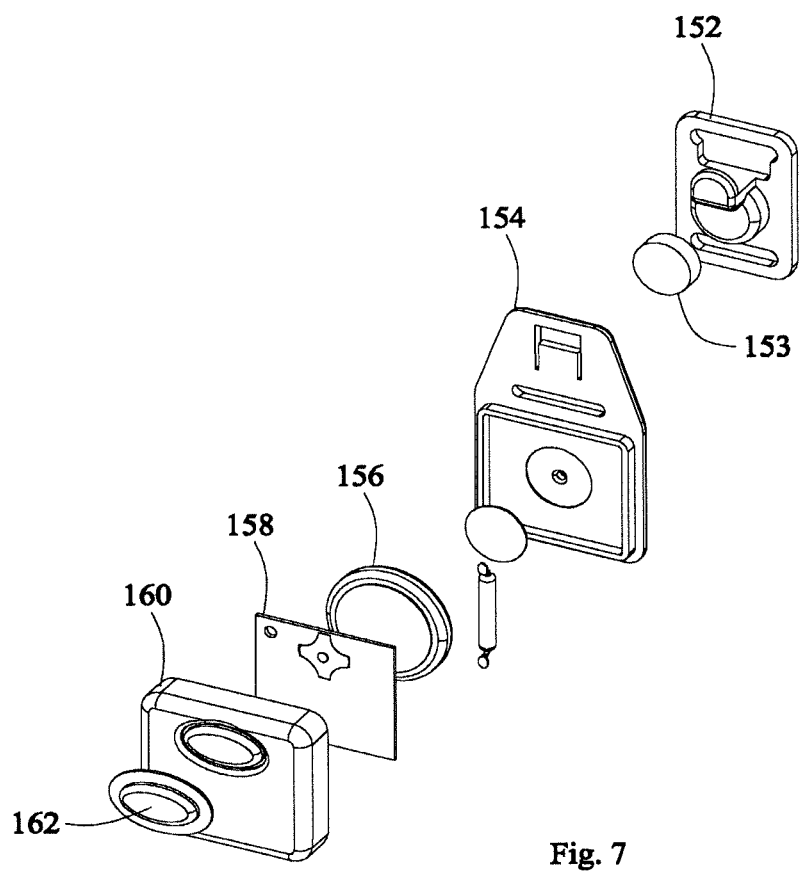
FIG. 7 is an exploded view of a computing device in accordance with an embodiment of the present invention.

As shown in FIGS. 1-5, according to several embodiments of the present invention, nursing garment computing system 100 includes a pairs of breast cups 102, where the breast cups 102 are unclasped or opened by means of clips 116, which are at least partially detachable from the shoulder strap 104. The clips 116 are configured for clasping each breast cup 102 with the shoulder straps 104 or for unclasping each breast cup 102 from the shoulder straps 104. Each clip is configured with a clasp sensor 140 that determines whether the breast cup 102 is open or closed. The clasp sensor 140 in the nursing garment is outfitted with the two magnetic sensors wired to a socket connection in a centralized location, or, optionally, in a non-centralized location. The clasp sensor 140 determines the status of a breast by generating sensor data that is being recorded by a miniature computing device 150. The computing device 150 records clasp sensor 140 data which is indicative of whether the breast cup is open or closed. As shown in FIG. 5, each clip 116 includes a first member 116a and a second member 116b, where the second member 116b is connected to the breast cup 102 and the first member 116a is connected to the shoulder strap 104 for clasping or unclasping the breast cups 102. The clasp sensor includes two magnetic sensors that are snap fit with each other when the breast cup 102 is clasped with the shoulder strap 104. One magnetic sensor 140 is configured with the first member 116a and another magnetic sensor 153 is coupled to the second member 116b of clip 116. In one embodiment, the breast cup 102 is partially detachable from the shoulder strap 104 by means of clip 116, the clip 116 is configured with the clasp sensor 140, such that, when the clip 116 is unclasped to lower a breast cup 102 for breastfeeding, the computing device 150 records the clasp sensor 140 data and stores the breastfeeding event within the memory of the computing device 150.

Figure 2:
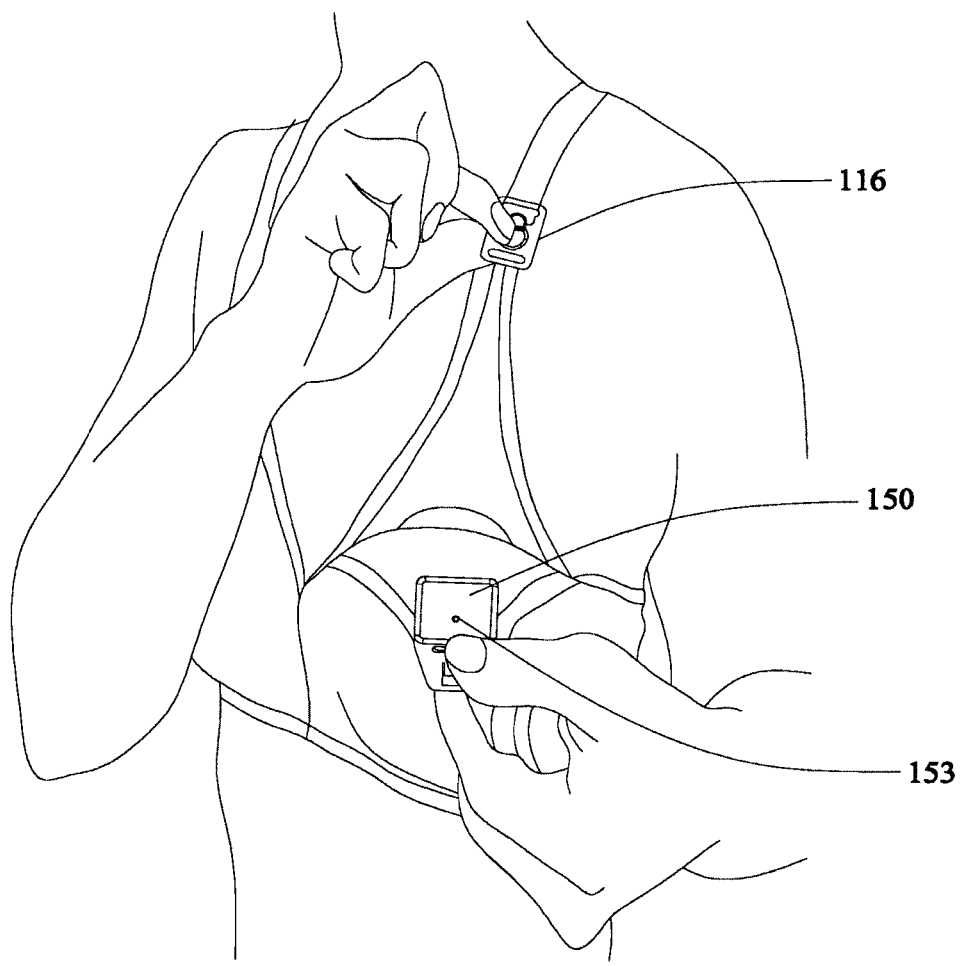
FIG. 2 is a perspective view of a nursing garment computing system, showing a breast cup open in accordance with an embodiment of the present invention.

As shown in FIGS. 2, 3, and 5, the clip 116 has two parts, the first member 116a and the second member 116b that are snapped together or otherwise attached. When beginning a breastfeeding event, the first member 116a is unclasped form the second member 116b that opens the breast cup 102. Once the nursing women is done breastfeeding the baby on opened side of breast, the second member 116b is clasped with the first member 116a. The amount of time that the breast cup 102 is opened is calculated as breastfeeding time. Once the clip 116 is clasped the computing device 150 records the amount of time the breast cup 102 has been open, the date and time of the breastfeeding event, and other pertinent data, and stores the data in the computing device 150. Users can then retrieve the data through a cell phone or other convenient device, or can transmit this information to a doctor or lactation consultant so the they can provide breastfeeding advice based upon more complete information that could be provided by the average breastfeeding woman keeping notes.

In one embodiment, the computing device 150 is configured to record and store clasp sensor data and further transmits to an external device such as a cell phone or other personal digital assistant device through Bluetooth® or another electronic communication means. In one embodiment, the external device is physically not connected to the nursing garment.

In a preferred embodiment, the computing device 150 may be configured to the body support or middle section 114. Further, in another embodiment the computing device 150 may be configured at different position near to the clips 116 based upon the convenience and comfort of the wearer as shown in FIGS. 3 and 4, the computing device 150 is attached on side portion 110. It should be noted that the location of the computing device 150 can be quite variable, as location on different parts of the invention will not change the overall function of the invention.

In one embodiment as shown in FIG. 2, the computing device 150 detects the clasp sensor 140 within a specified, pre-programmed distance, such that when the clip 116*b* is unclasped and lowered for breastfeeding, the computing device 150 records the amount of time the breast cup 102 is open. The computing device 150 has capabilities that can sense the clasp sensor 140 within a certain distance, whereupon the computing device 150 will begin recording time that the breast cup 102 is open. For example, when the breast cup 102 is at attached configuration, as shown in FIG. 4, the distance between clasp sensor 140 and the computing device 150 is a shorter distance (called Attached distance 132*a*), than when the breast cup 102 is opened and the clasp sensor 140 is further from the computing device 150 (called Detached distance 132*b*), as can also be seen in FIG. 5. Thus, computing device 150 is programmed to start counting as "breastfeeding time" whenever the distance between the clasp sensor 140 and the computing device 150 is Detached Distance 132*b*. In an alternate embodiment, the amount of breastfeeding time can be calculated without the use of wires 125. Because the clasp sensor 140 has its own electronic identity for each breast cup 102, the computing device 150 can keep track of which breast cup 102 has been unclasped for breastfeeding for different time spans, time between nursing periods, time of nursing periods for each side, a record of which side was nursed last, and a record of which side was nursed first during the last breastfeeding event.

Further in another embodiment as shown in the FIG. 5 illustrate how the clasp sensor 140 can trigger the beginning or ending of a breastfeeding event through its movement either toward or away between the magnetic sensors 140*a*, 140*b*. In this case, the magnetic sensor 140*b* has been moved away from the magnetic sensor 140*a* enough of a distance to start the timing of a breastfeeding event. Alternatively, distances 132*a*, 132*b* can also indicate how close clasp sensor 140 has to get to trigger the timer, or alternatively, how far away sensor 140 has to be to trigger, or stop, the timer. It should be noted that the invention works equally well if the distances 132*a*, 132*b* are measured with clasp sensor 140 being further away from, or closer to either the claps sensor 140 on the shoulder strap 104 or near the computing device 150.

In another embodiment, when a breast cup 102 is opened for breastfeeding, in the breastfeeding event, the second member 116*b* is unclasped form the first member 116*b* to open the breast cup 102. Once the nursing women is done breastfeeding the baby on the opened breast, the first member 116*a* is clasped with the second member 116*b*. In an exemplary embodiment, the second member 116*b* of the breast cup 102 clasps over the first member 116*a* of the shoulder strap 104. The clasping means snap such that they attach the second member 116*b* of the breast cup 102 to the first member 116*a* of the shoulder strap 104. Further, it is appreciated that the second member 116*b* of the clip 116 clasps over the first member 116*a* of the clip 116 to removably secure the breast cup 102 to the shoulder strap 104. In one embodiment, when the breast cup 102 is opened, thus starting to count the time as breastfeeding time. In another embodiment calls for the timer to stop once the clasped sensor 140 is within a certain distance of the computing device 150. It is contemplated that the use of sensors to "start" and "stop" the counting of time during which breastfeeding and/or pumping of milk is accomplished. These records are kept electronics for not only the mother to allow her to remember the during of her breastfeeding events, but also to let her transmit that data to her doctor and lactation consultants to that they can advise her from a background of more complete data than if they had only her notes to rely upon.

Further in some embodiment's calls for the clip 116 to be made of two transmitting portions, where once the clip 116 is opened to pull down a breast cup 102, the computing device 150 recognizes that the breast cup has been pulled down for breastfeeding, and will begin to record the time, and, when the breast cup has been pulled back up the computing device 150 recognizes that the breastfeeding event has ended. It is also contemplated that clips 116 may be preferably magnetic and made of stainless steel, and it is also contemplated that any and, optionally, all electronic components can be coated with a plastic coat to enhance the machine washability of the nursing garment.

As shown in the FIG. 6, FIG. 7, FIG. 8 and FIG. 9, in a preferred embodiment, the computing device 150 also functions as a lactation sensor and is a water-resistant micro electronic device comprised of a microprocessor, an external magnetic switch 151, and internal clock 198, and data storage components 190. It is further equipped with Bluetooth communications 192 for data access and designed to be sewn into any nursing garment. As described above, the computing device 150 is a miniature electronic device that is attached to the nursing garment in order to keep track of the breastfeeding time and breastfeeding event.

In a preferred embodiment as shown in FIG. 6, FIG. 7, FIG. 8 and FIG. 9 the nursing garment is outfitted with a computing device 150 that includes a magnetic sensor switch 151. The computing device 150 when connected to the nursing garment will record changes in the status of the external sensor 140, on the internal memory device allowing the recoding date, time and status of the switch 151, into a data file for downloading via a Bluetooth connection 192. As described above, the external sensor 140, is a magnetic sensor configured with the clips 116. The magnetic sensor switch 151, may be designed with SPST magnetic reed switch (No) sewn into various key locations, or may be attached to the various plastic clips and other parts of the bra. Each switch 151 will be coupled with an opposing mini neodymium magnet in a configuration that when the breast cup 102 is open the SPST magnetic reed switch will be moved to the closed position. Switch 151*a* is a SPST (No)

Momentary contact switch depressing the button for 3 or more seconds changes the operational status of the computing device 150 from on to off or off to on. Switch 151*b* a SPST (No) Momentary contact switch depressing the button for three or more seconds changes the configuration status of the Bluetooth device from open to closed allowing for external device setup.

The computing device 150 includes a fastener clip 152, a bottom cover 154, a battery 156, electric circuit board 158, main cover 160 and a LED button 162 that are housed as an enclosed portable miniature device. As described above, such clasp sensor data may be analyzed to determine breastfeeding time and breastfeeding event. It should be appreciated that the fastener clip 152 of the computing device 150 described herein may be embodied as one or more hooks, snaps, loops, Velcro strips, ties, magnets, self-releasing adhesive strips, buttons, and/or any other suitable fasteners so that the commuting device 150 may be attached to a nursing garment.

Further, on the main cover 160 the Led button 162 is equipped with a display/status. The status of Led button is displayed in varying color for example Red, Green, Blue. The Led Button 162 is Low power, low luminance Light emitting diode. Further, in exemplary, the Led button will display in green color for at least ten second than fade to off when the computing device 150 is on. In switching off the computing device 150 may flash red colors three times.

Figure 8:
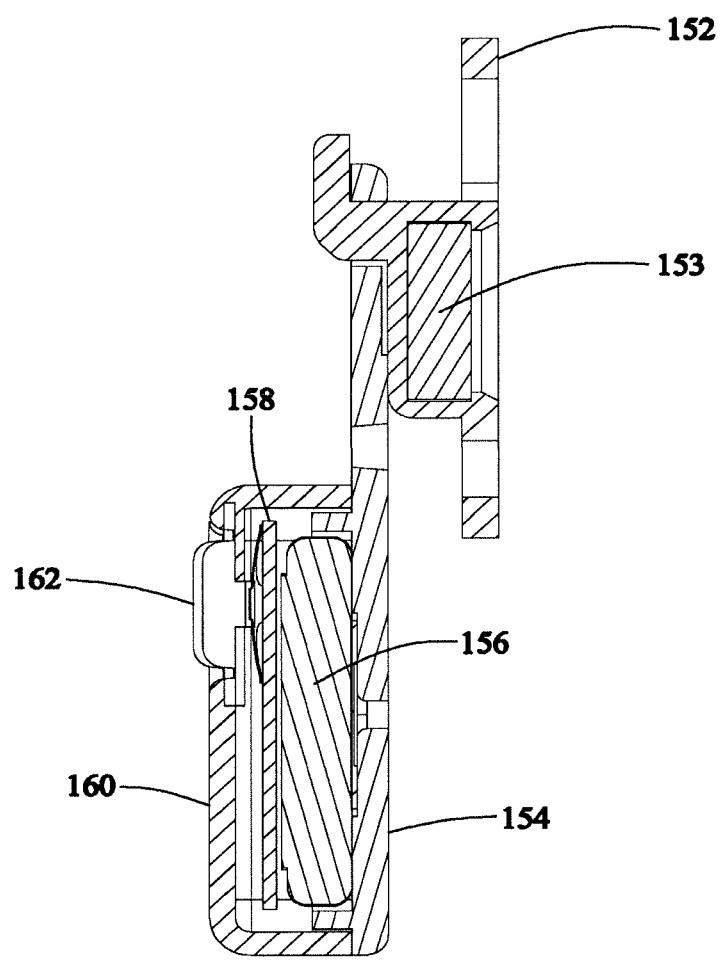
FIG. 8 is another perspective view of a computing device in accordance with an embodiment of the present invention.

In the cross-sectional view as shown in FIG. 8, the computing device 150 may include a fastener clip 152, a bottom cover 154, a battery 156, electric circuit board 158, main cover 160 and a LED button 162. The fastener clip 152 further includes a magnet 153. Each switch 151*a*, 151*b* will be coupled with an opposing mini neodymium magnet 153 in a configuration that when the breast cup 102 is open the SPST will be moved to the closed position, and when closed, the SPST will move into the open position.

Figure 9:
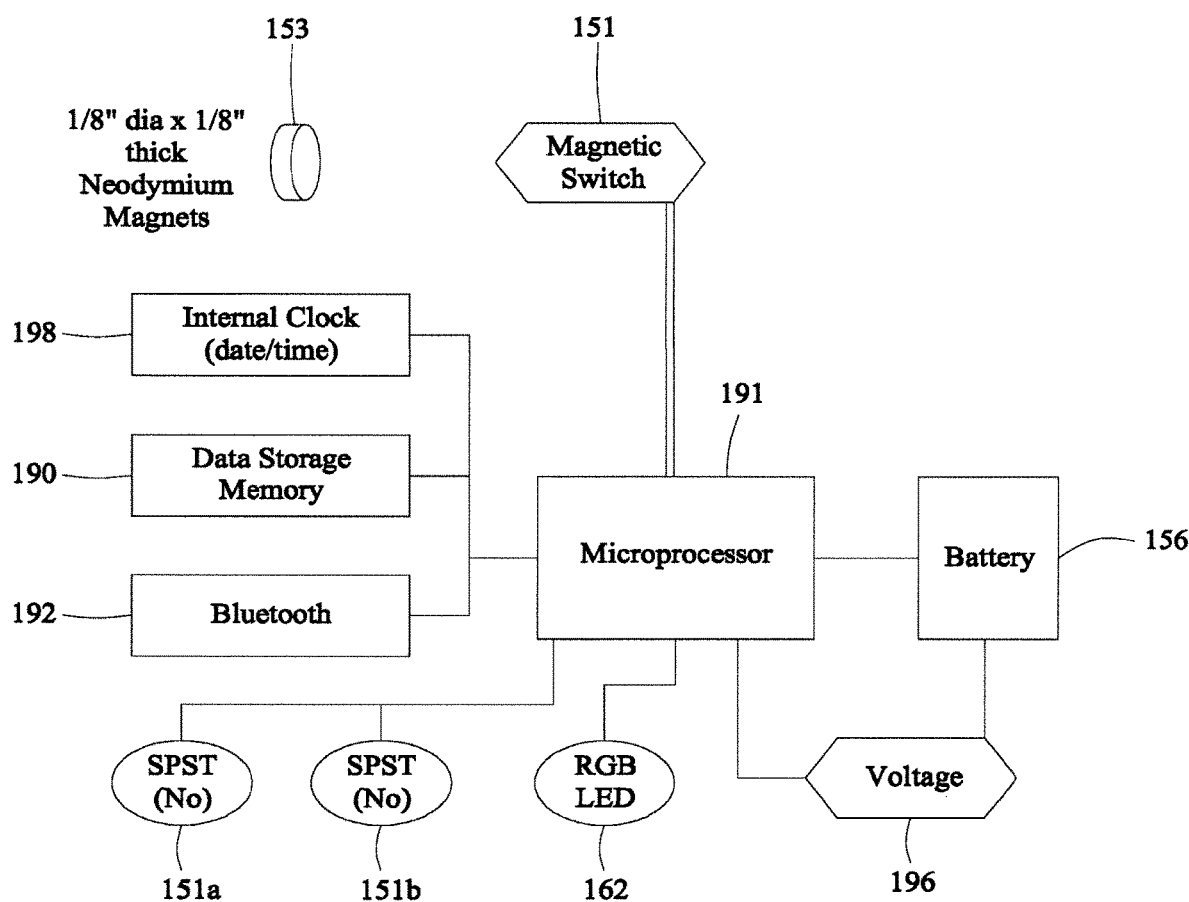
FIG. 9 is a schematic of the electrical circuit in the computing device in accordance with an embodiment of the present invention.

Further, as shown in FIG. 9, the computing device 150 may include a flash memory (data storage memory) 190; the flash memory 190 is internal non-volatile memory that store status of sensors and device operation. The status data report will be transferred in Fat32 format with ASCII Text file in a CSV format is preferred for ease of data transfer. Each data file may begin at 00:00:01 of a local day and be named YYMMDD. CSV and contain one line per event with bits of (HH:MM:SS, sensor, action). For Example: 00:02:23, 1,0 represents switch one open, 00:26:45, 1,1 represents switch one closed, 03:56:02,2,0 represents switch two open and 04:03:51, 2,1 represents switch two closed. This is merely an example of the present invention is not limited in its application to the details of construction and arrangement of the parts illustrated in the drawings.

Figure 10:
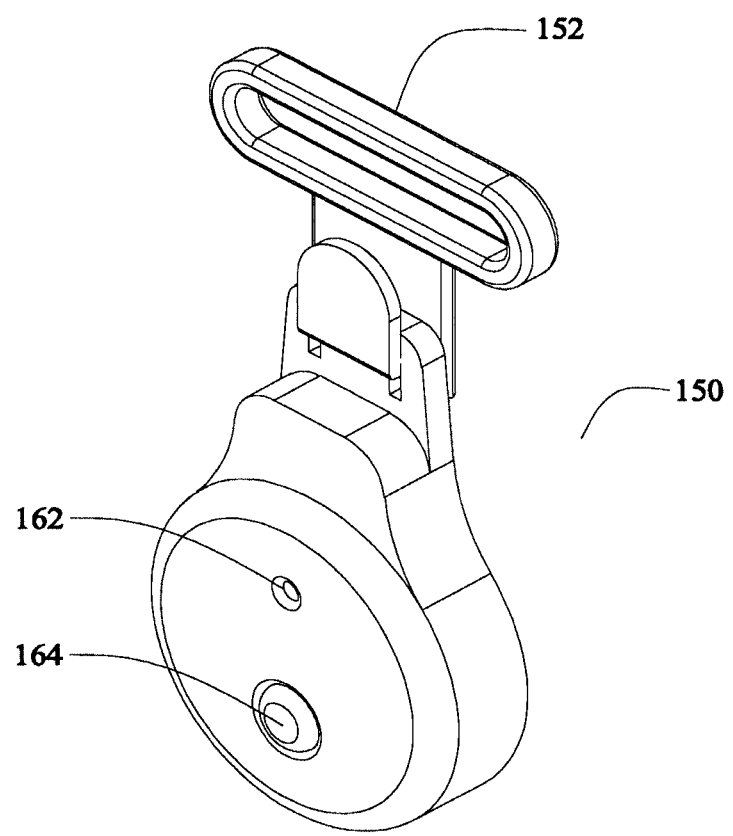
FIG. 10 is another perspective view of a computing device in accordance with an embodiment of the present invention.
Figure 11:
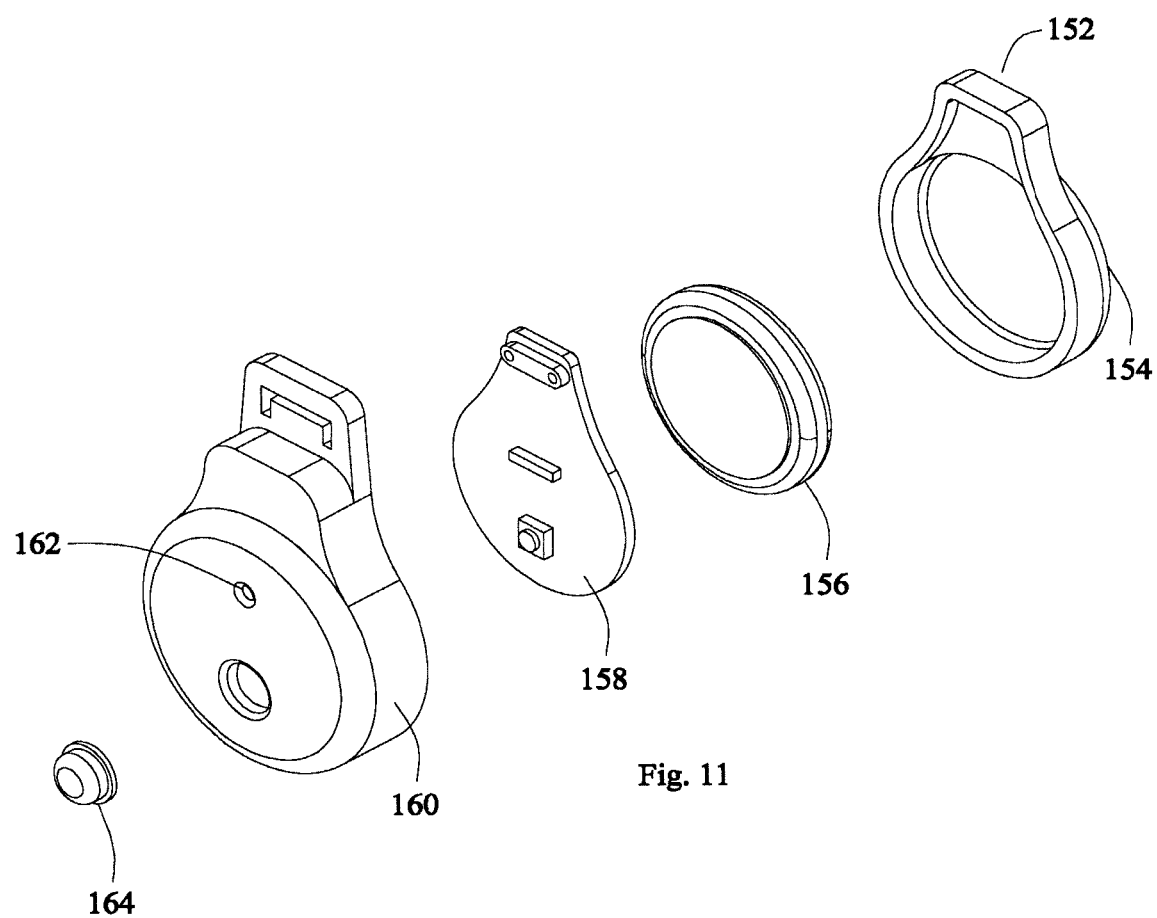
FIG. 11 is an exploded view of a computing device in accordance with another embodiment of the present invention.

Further, the computing device 150 shown in FIG. 10 and FIG. 11 includes an electric circuit board 158, an input/output ("I/O"), a main cover 160, an LED button 162, and memory for data storage 192, a communication circuitry, and one or more sensors. Of course, the computing device 150 may include other or additional components, such as those commonly found in a typical computing device in other embodiments. In the illustrative embodiment, the computing device 150 is integrated with the nursing garment. In other embodiments, the computing device may be embodied as a nursing kit such that the computing device 150 may be secured to, for example, a traditional nursing garment.

The microprocessor may be embodied as any type of processor capable of performing the functions described herein. For example, the microprocessor may be embodied as a single or multi-core processor(s), digital signal processor, microcontroller, or other processor or processing/controlling circuit. It should be appreciated that the memory may be embodied as any type of volatile or non-volatile memory or data storage capable of performing the functions described herein. In some embodiments, the computing device 150 may form a portion of a chip and be incorporated on a single integrated circuit chip. In a preferred embodiment, the computing device 150 includes an internal real-time clock 198 that will include a real time clock for data tracking/logging operations. Real time clock may be a stand-alone chip or a function of the microprocessor.

Further, the computing device 150 may include a Voltage sensor 196 that may self-monitor the status of its rechargeable battery utilizing a voltage (or similar) sensor on its rechargeable battery. Further, as described above, the computing device 150 is programmed; therefore the microprocessor code will monitor the value of the battery and notify the user of low power condition by flashing the Led button 162.

Further, the Bluetooth connection 192 may be equipped with a low energy Bluetooth system to allow for the external connection to the device by IDE on iPhone and android devices.

In alternate embodiment, the computing device 150 as shown in the FIG. 10 and FIG. 11 includes a fastener clip 152, a bottom cover 154, a battery 156, electric circuit board 158, main cover 160, a LED button 162 and Bluetooth button 164 that are housed as an enclosed portable miniature device. As described above, such clasp sensor data may be analyzed to determine breastfeeding time and breastfeeding event. It should be appreciated that the Bluetooth button 164 is used for Bluetooth pairing with other external device as described herein may be embodied as a mobile device or computer.

Figure 12:
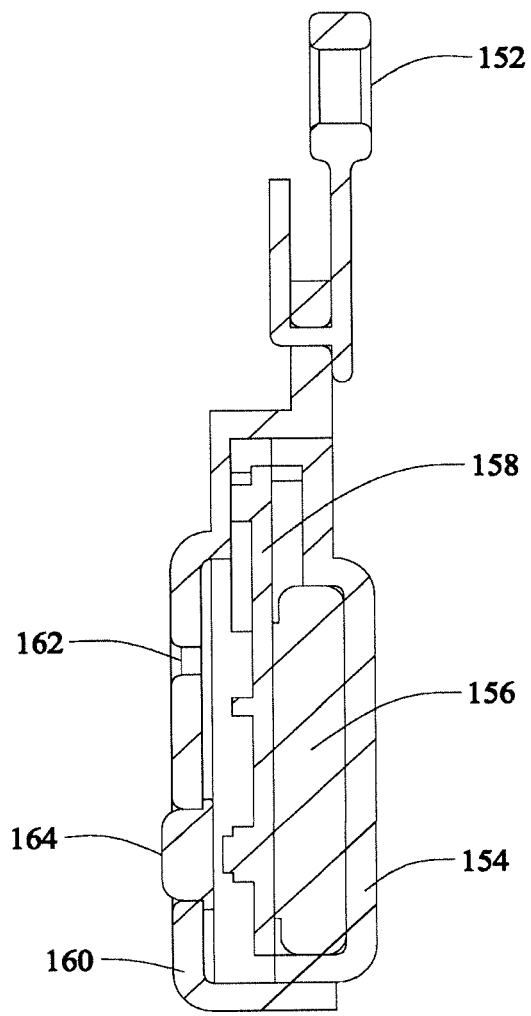
FIG. 12 is a cross-sectional view of the computing device of FIG. 8 in accordance with an embodiment of the present invention.

In the cross-sectional view as shown in the FIG. 12, the computing device 150 may include a fastener clip 152, a bottom cover 154, a battery 156, electric circuit board 158, main cover 160 and a LED button 162.

Figure 13:
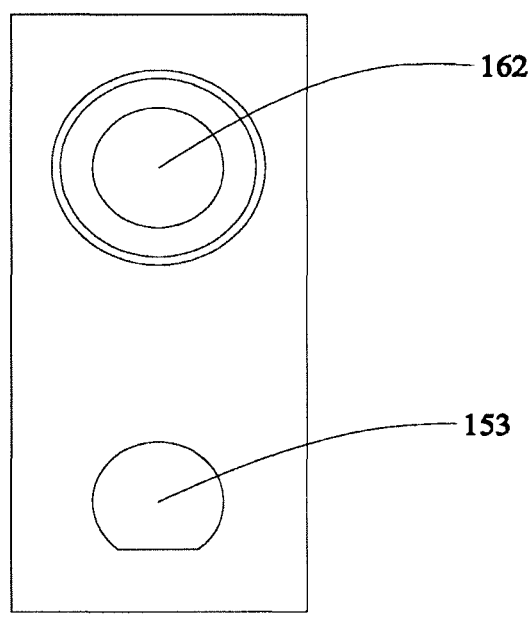
FIG. 13 is a front sectional view of the clip arrangement with the computing device in accordance with the present invention.

Further, the LED button 162 and the magnetic sensor 153 of the computing device 150 are shown in the cross-sectional view as shown in the FIG. 13.

In one embodiment, the computing device 150 is water and dirt resistant.

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

REFERENCE NUMBERS USED

100 Nursing garment computing system
102 Breast cups

104 Shoulder straps
116 Clips
116a First member
116b Second member
140 Clasp sensor
150 Computing device
151 Magnetic switch
151a, 151b SPST magnetic reed switch (NO)
152 Fastener clip
153 Magnetic sensor
154 Bottom cover
156 Battery
158 Electric circuit board
160 Main cover
162 LED button
164 Bluetooth button
190 Data storage components (Flash memory)
191 Microprocessor
192 Bluetooth communications
196 Voltage sensor
198 Internal clock

The invention claimed is:

1. A system for breastfeeding comprising:
a nursing bra having a shoulder strap and at least one portion which can be selectively moved between a first position covering a breast of a woman and a second position not covering the breast of the woman;
a sensor attached to the at least one portion and configured to detect a nursing period only when the at least one portion is in the second position and at least a predetermined distance from the shoulder strap; and
a computing unit establishing an elapsed time in which the at least one portion is in the second position to establish the nursing period.

2. The system of claim 1, wherein the at least one portion of the garment comprises a cup portion of the bra.

3. The system of claim 2, wherein the bra includes a clip for selectively, removably detaching the cup portion from the shoulder strap, wherein the sensor detects when the cup portion is detached from the shoulder strap.

4. The system of claim 3, wherein at least part of the sensor is provided on the clip.

5. The system of claim 4, wherein part of the sensor is attached to the shoulder strap, and another part of the sensor is attached to the cup so as to be detachable from the shoulder strap.

6. The system of claim 1, wherein the at least one portion of the garment comprises a first cup portion of the bra and the bra includes a second cup portion, the system including another sensor for detecting when the second cup portion is in a position exposing another breast of the woman, and wherein the computing unit is further configured to establish a feeding side of the nursing bra.

7. The system of claim 1 further comprising a cell phone, wherein the computing unit is part of the cell phone.

8. The system of claim 7, wherein the cell phone is connected to the sensor via a wireless connection.

9. The system of claim 8, wherein the sensor includes an actuator for Bluetooth pairing the sensor to the cell phone.

10. The system of claim 1, wherein the computing unit is external from the garment.

11. The system of claim 1, wherein the sensor is water resistant so as to be functional upon washing the garment.

12. A system for tracking a breastfeeding event comprising:
a sensor attached to at least one portion of a nursing bra which can be selectively moved between a first position covering a breast of a woman and a second position not covering the breast of the woman, said sensor configured to detect the breastfeeding event including a nursing period detected only when the at least one portion is in the second position and at least a predetermined distance from the shoulder strap; and
a computing unit, in communication with the sensor, establishing an elapsed time in which the at least one portion is in the second position to establish the nursing period and configured to record data on the breastfeeding event.

13. A method of tracking a nursing event comprising:
sensing exposure of a nursing woman's breast with a sensor by detecting when at least one portion of a nursing bra is selectively moved from a first position covering the breast to a second position not covering the breast and at least a predetermined distance from a shoulder strap of the nursing bra; and
recording data on the nursing event based on signals from the sensor including establishing, with a computing unit, an elapsed time in which the at least one portion is in the second position to establish the nursing period only during the exposure.

14. The method of claim 13, wherein the data is recorded on a cell phone.

15. The method of claim 13, wherein sensing exposure of the nursing woman's breast comprises sensing movement of a first cup portion of a nursing bra to expose the nursing woman's breast, with the nursing bra further including a second cup portion which can be moved to expose another breast of the nursing woman, and wherein the data includes a feeding side of the nursing bra.

16. The method of claim 13, wherein the data includes the elapsed time of the nursing event.

17. The method of claim 13, wherein the data is recorded using a wireless connection.

18. The method of claim 17, wherein the data is recorded using a cell phone.

* * * * *